(12) United States Patent
Haddock et al.

(10) Patent No.: US 11,435,306 B2
(45) Date of Patent: Sep. 6, 2022

(54) QUANTIFYING EMULSIFIED ASPHALT-BASED CHIP SEAL CURING TIMES USING ELECTRICAL PROPERTIES

(71) Applicant: Purdue Research Foundation, West Lafayette, IN (US)

(72) Inventors: John Ernest Haddock, Williamsport, IN (US); William Jason Weiss, Corvallis, OR (US); Miguel Angel Montoya Rodriguez, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 514 days.

(21) Appl. No.: 16/532,539

(22) Filed: Aug. 6, 2019

(65) Prior Publication Data

US 2020/0049642 A1    Feb. 13, 2020

Related U.S. Application Data

(60) Provisional application No. 62/715,731, filed on Aug. 7, 2018.

(51) Int. Cl.
*G01N 27/04* (2006.01)
*G01N 33/18* (2006.01)
(Continued)

(52) U.S. Cl.
CPC ......... *G01N 27/048* (2013.01); *G01N 27/30* (2013.01); *G01N 33/18* (2013.01); *C08L 95/00* (2013.01)

(58) Field of Classification Search
CPC ...... G01N 27/048; G01N 27/30; G01N 33/18; G01N 27/226; G01N 27/223; C08L 95/00
See application file for complete search history.

(56) References Cited

U.S. PATENT DOCUMENTS

2008/0246489 A1* 10/2008 Coster ................ G01N 15/1031
324/446
2014/0098458 A1* 4/2014 Almadhoun ............. H01G 4/14
361/305

(Continued)

OTHER PUBLICATIONS

Needham, "Developments in Bitumen Emulsions Mixtures for Roads," Ph.D. dissertation, University of Nottingham, Nottingham, United Kingdom, 1996.

(Continued)

*Primary Examiner* — Huy Q Phan
*Assistant Examiner* — Zannatul Ferdous
(74) *Attorney, Agent, or Firm* — Piroozi-IP, LLC

(57) ABSTRACT

A method of determining moisture content in an emulsified asphalt-aggregate system is disclosed. The method includes: placing a first electrode in an emulsified asphalt-aggregate system (Mixture) at a first depth, placing a second electrode in the Mixture at a second depth, applying an alternating current (AC) signal between the first electrode and the second electrode, measuring impedance, determining the frequency which yields the minimum measured impedance, recording the minimum measured impedance, repeating the above steps at a predetermined time interval until the recorded minimum impedance is about 10 times of the first recorded minimum impedance, and alerting a user that the Mixture has sufficiently cured.

20 Claims, 9 Drawing Sheets

(51) Int. Cl.
G01N 27/30 (2006.01)
C08L 95/00 (2006.01)

(56) References Cited

U.S. PATENT DOCUMENTS

| | | | | |
|---|---|---|---|---|
| 2014/0182362 | A1* | 7/2014 | Potyrailo | G01N 27/026 |
| | | | | 73/64.53 |
| 2016/0320516 | A1* | 11/2016 | Clark | G01V 3/24 |
| 2017/0131226 | A1* | 5/2017 | Boul | G01N 33/383 |
| 2020/0101456 | A1* | 4/2020 | Watkins | B01L 3/50273 |
| 2020/0227829 | A1* | 7/2020 | Jouanlanne | H01Q 9/0407 |

OTHER PUBLICATIONS

Shahidi, "An Electrochemical Impedance Spectroscopic Diagnostic Device for Characterization of Liquid-Liquid Systems and Phase Separation Detection in Emulsions", M.Sc. Dissertation, Department of Mechanical Engineering, University of Alberta, Edmonton, Alberta, 2013.
Shuler, S., "When to Broom or Remove Traffic Control Safely on Fresh Emulsified Asphalt Chip Seals," Journal of the Transportation Research Board, No. 2235, 2011, pp. 82-87.
Shuler et al., "Manual for Emulsion-Based Chip Seals for Pavement Preservation," NCHRP Report 680, Transportation Research Board, Washington, D.C., 2011.
Sowa et al., "Electrical Properties of Bitumen Emulsions," Fuel, vol. 74, No. 8,1995, pp. 1176-1179.
Spragg et al., "Electrical Properties of Cementitious Systems: Formation Factor Determination and the Influence of Conditioning Procedures," Advances in Civil Engineering Materials, vol. 5, No. 1, 2016, pp. 124-148.
Takamura et al., "Paving with Asphalt Emulsions," Advances in Asphalt Materials, Road and Pavement Construction, Woodhead Publishing Series in Civil and Structural Engineering, No. 56, Elsevier Ltd, United Kingdom, 2015, pp. 393-426.
Texas Department of Transportation, "Seal Coat and Surface Treatment Manual," Austin, TX, 2003.
Wegman, "Design and Construction of Seal Coats," Report No. 9LRR661, Minnesota Department of Transportation, Mendota Heights, MN, 1991.
Asphalt Institute, Asphalt Emulsion Manufacturers Association, "A Basic Asphalt Emulsion Manual," Manual Series No. 19, Third Edition, USA, 2008.
Banerjee, "Breaking and Curing Rates in Asphalt Emulsions", Ph.D. Dissertation, The University of Texas at Austin, Austin, TX., 2012.

Baumgardner, "Asphalt Emulsion Manufacturing Today and Tomorrow," Transportation Research Circular E-C102: Asphalt Emulsion Technology, Washington, D.C., 2006, pp. 16-25.
Booth et al., "Development of Very High Bitumen Content Emulsions for Sprayed Sealing," Proceedings 17th ARRB Conference, Gold Coast, Australian Road Research Board, Part 3, 1994. pp. 73-89.
Bu et al., "Using Fick's Second Law and Nernst-Planck Approach in Prediction of Chloride Ingress in Concrete Materials," Advances in Civil Engineering Materials, vol. 3, No. 1, 2014, pp. 566-585.
Dukhin et al., "How non-ionic "electrically neutral" surfactants enhance electrical conductivity and ion stability in non-polar liquids," Journal of Electroanalytical Chemistry, vol. 588, No. 1, 2006, pp. 44-50.
Gransberg et al., "Chip Seal Best Practices, A Synthesis of Highway Practice," NCHRP Synthesis 342, Transportation Research Board, Washington, D.C., 2005.
Howard et al., "Correlation of Moisture Loss and Strength Gain in Chip Seals," Journal of the Transportation Research Board, No. 2207, 2011, pp. 49-57.
James, "Overview of Asphalt Emulsion," Transportation Research Circular E-C102: Asphalt Emulsion Technology, Washington, D.C., 2006, pp. 1-15.
Lee et al., "Performance Evaluation of Seal Coat Materials and Designs", Report No. FHWA/IN/HTRP-2011/05, Joint Transportation Research Program, Indiana Department of Transportation and Purdue University, West Lafayette, IN, 2011.
Lee et al., "Effect of Electrical Surface Charge on Seal Coat Curing and Aggregate Loss Performance," Journal of Testing and Evaluation, vol. 44, No. 4, 2016, pp. 1661-1670.
Montoya et al., "Using Electrical Resistance to Evaluate the Chip Seal Curing Process", Road Materials and Pavement Design, vol. 18, sup. 4, Date 2017 exact date Unknown pp. 98-111.
Montoya et al., "Quantifying asphalt emulsion-based chip seal curing times using electrical resistance measurements," Joint Transportation Research Program, West Lafayette, IN: Purdue University. 2017 exact date Unknown.
Montoya et al., "Quality control tool for asphalt emulsion-based chip seal curing times," Bearing Capacity of Roads, Railways and Airfields—Proceedings of the 10th International Conference on the Bearing Capacity of Roads, Railways and Airfields, BCRRA 2017 exact date Unknown, 603-608.
Mukherjee et al., "Assessment of Moisture Diffusion Distance in Pressboard Insulation Within Transformer Using Fick's Law," 2014 Eighteenth National Power Systems Conference, Dec. 2014, pp. 1-4.

* cited by examiner

QUANTIFYING EMULSIFIED ASPHALT-BASED CHIP SEAL CURING TIMES USING ELECTRICAL PROPERTIES

CROSS-REFERENCE TO RELATED APPLICATIONS

The present patent application is related to and claims the priority benefit of U.S. Provisional Patent Application Ser. No. 62/715,731 filed 7 Aug. 2018, the contents of which are hereby incorporated by reference in its entirety into the present disclosure.

TECHNICAL FIELD

This present disclosure relates to the measurement of moisture content in a pavement material based on measuring real and imaginary parts of electrical impedance.

BACKGROUND

This section introduces aspects that may help facilitate a better understanding of the disclosure. Accordingly, these statements are to be read in this light and are not to be understood as admissions about what is or is not prior art.

As pavements age, periodic preservation is required. A typical preservation approach is the chip-seal method, whereby an emulsified asphalt film with aggregate chips embedded therein is provided over an existing pavement. The chip seal method is also known as a seal coat, asphalt surface treatment, single surface treatment, bituminous surface treatment, sprayed seal, surfacing seal, or surface dressing. The emulsified asphalt contains water, and the evaporation of water plays an important role in the curing of the chip seal system.

Typically, traffic is rerouted at a great cost to travelers while a segment of pavement is being sealed. Hence, the length of time whereby traffic is being rerouted is a critical factor and must be minimized to avoid negative impact such rerouting creates. In addition, sealing crews require mechanized sweeper to sweep any loose aggregate. All of these delays play havoc with traffic patterns. Therefore, there is a urgency to resume traffic, resulting in sometimes resuming use of the pavement prior to proper curing. However, not allowing sufficient curing time can adversely affect the seal thereby weakening it, resulting in decreased performance and even premature failure.

The necessary field curing time of a chip seal is dependent on many factors, such as wind speed, humidity, temperature, etc. Currently, there is no streamlined quantitative approach to field measure the moisture content in chip seal systems. Sealing crews use empirical factors based on experience. Furthermore, even to an experienced seal crew member, while these empirical factors convey a conclusion of proper curing, there may be a hidden layer of water underneath the emulsified asphalts-aggregate systems that can result in the same premature failures.

Therefore, there is an unmet need for a novel streamlined quantitative approach to enable a seal crew to know when sufficient curing of an emulsified asphalt has taken place.

SUMMARY

A method of determining moisture content in an emulsified asphalt-aggregate system is disclosed. The method includes placing a first electrode in an emulsified asphalt-aggregate system (Mixture) at a first depth (step A). The method also includes placing a second electrode in the Mixture at a second depth (step B). The method also includes applying an alternating current (AC) signal between the first electrode and the second electrode (step C). The method also includes measuring impedance, comprising of a real component representing resistance between the first electrode and the second electrode and an imaginary component representing capacitance between the first electrode and the second electrode (step D). The method also includes determining the frequency which yields the minimum measured impedance (step E). The method also includes recording the minimum impedance (F). The method also includes repeating steps C-F at a predetermined time interval until the recorded minimum impedance is about 10 times of the first recorded minimum impedance. The method further includes alerting a user that the Mixture has sufficiently cured.

A system for determining moisture content in an emulsified asphalt-aggregate system is also disclosed. The system includes a first electrode adaptable to be placed in an emulsified asphalt-aggregate system (Mixture) at a first depth. The system also includes a second electrode adaptable to be placed in the Mixture at a second depth. Furthermore, the system includes an alternating current (AC) source adaptable to provide an AC signal between the first electrode and the second electrode at a plurality of frequencies. Additionally, the system includes an impedance measurement device adaptable to measure impedance between the first electrode and the second electrode, the impedance comprising of a real component representing resistance between the first electrode and the second electrode and an imaginary component representing capacitance between the first electrode and the second electrode. The system also includes a processing unit. The processing unit is adapted to determine the frequency which yields the minimum measured impedance (Step A). The processing unit is also adapted to record the minimum measured impedance. Additionally, the processing unit is configured to repeat steps A-B at a predetermined time interval until the recorded minimum measured impedance is about 10 times of the first recorded minimum measured impedance. The processing unit is then adapted to alert a user that the Mixture has sufficiently cured.

DETAILED DESCRIPTION

Figure 1A:
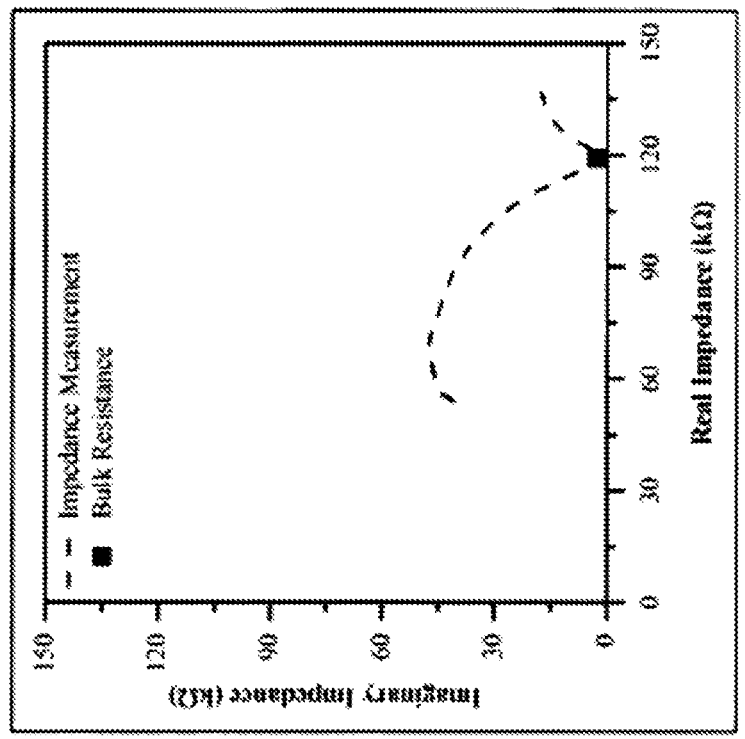
FIG. 1(a) is phasor diagram of the real and imaginary components of impedance.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In the present disclosure, the term "about" can allow for a degree of variability in a value or range, for example, within 10%, within 5%, or within 1% of a stated value or of a stated limit of a range.

In the present disclosure, the term "substantially" can allow for a degree of variability in a value or range, for example, within 90%, within 95%, or within 99% of a stated value or of a stated limit of a range.

A novel streamlined quantitative approach is presented to enable a pavement field worker to know when an emulsified asphalt system has sufficiently cured. A system capable of providing a frequency sweep with a two-point uniaxial Electrical Impedance Spectroscopy (EIS) testing is used to determine electrical properties of an emulsified mixture including aggregates. Using this system quantitative measurements were performed that are used to provide a correlation between the amount of curing that has occurred and electrical properties of the mixture.

The water in the emulsified mixture provides a highly polar system comprising various ionic species (i.e., free emulsifier, calcium chloride, sodium chloride), making it well suited for measuring electrical impedance since a person having ordinary skill in the art appreciates polar compounds (i.e., ionized water) are reasonable conductors of electricity, whereas nonpolar compounds (i.e., asphalt) typically behave as insulators. Therefore, as water evaporates, the effect of free ions responsible for providing conductivity decreases, thereby increasing the mixture impedance. It should be appreciated that Non-polar solvents generally create an unfriendly environment for ions, which in turn leads to a low conductivity of such non-polar solvents, typically five orders of magnitude less than that of water.

Figure 1B:
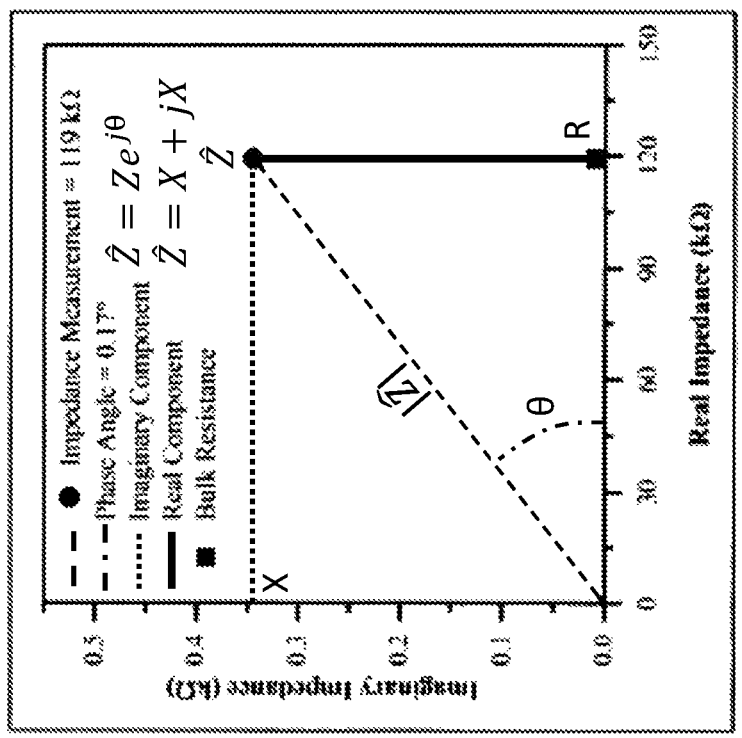
FIG. 1(b) is a Nyquist diagram of the real and imaginary components of impedance.
Figure 1C:
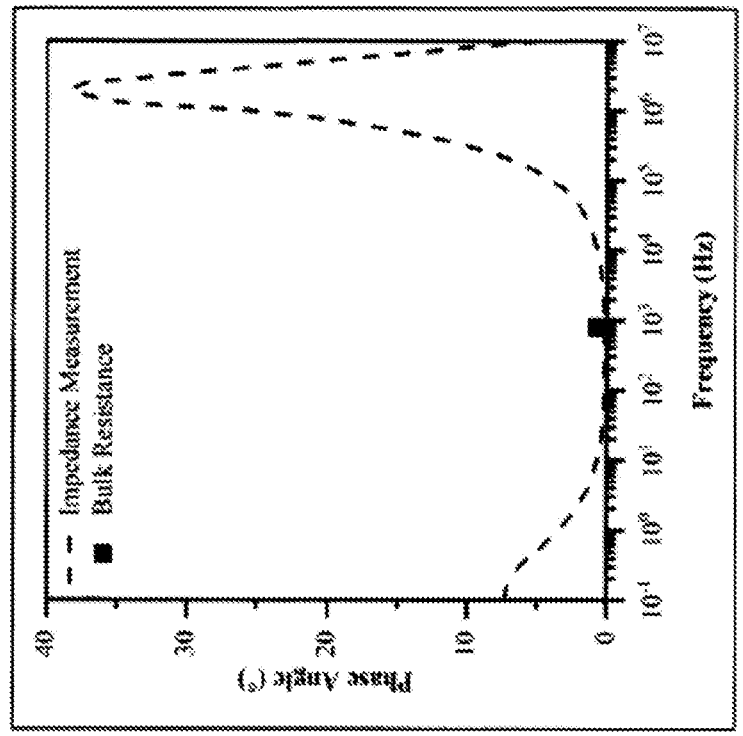
FIG. 1(c) is a graph of impedance vs. frequency.
Figure 1D:
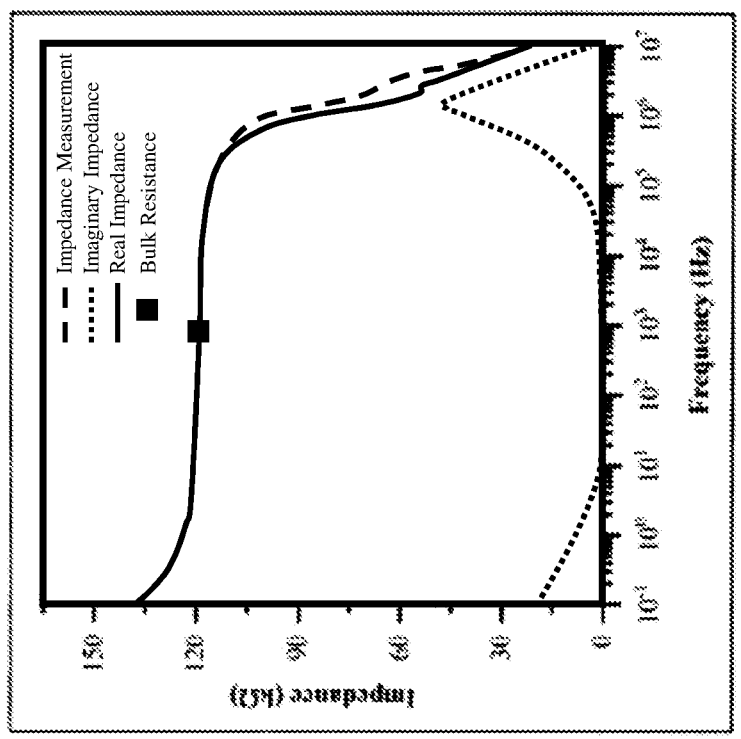
FIG. 1(d) is a graph of phase angle vs. frequency.

An impedance/gain-phase analyzer was used to assess the electrical properties of an emulsified asphalt-aggregate mixture. An alternating current (AC) is applied between two probes at various frequencies and impedance (Z) which includes both a real component (due to electrical resistance between probes) and an imaginary component (due to the capacitance between the two probes) is measured. Referring to FIGS. 1(a) and 1(b) these real and imaginary components are depicted with respect to each other (in the form of a phasor diagram (FIG. 1(a)) and in the form of a Nyquist diagram (FIG. 1(b))) and with respect to frequency (impedance vs. frequency (FIG. 1(c)), and phase angle v. frequency (FIG. 1(d)).

It should be appreciated that the magnitude and phase angle of the impedance varies based on the AC signal's frequency. Here, a frequency range between $10^{-1}$ and $10^7$ Hz was applied. Within this frequency range, the impedance measurement with the minimum imaginary component, having the lowest absolute value of phase angle, was identified which yields the bulk resistance (i.e., an impedance with minimum imaginary component is about the same as bulk resistance). FIG. 1(b) shows a typical Nyquist plot, which identifies the bulk resistance. The Nyquist plot represents the set of imaginary and real impedance components measured over the frequency range. The Bode plots (one for impedance (FIG. 1(c)) and one for phase angle (FIG. 1(d))) provide the frequency (or frequency range) at which the lowest absolute value of phase angle can be obtained (i.e., about $10^3$ Hz).

Figure 2:
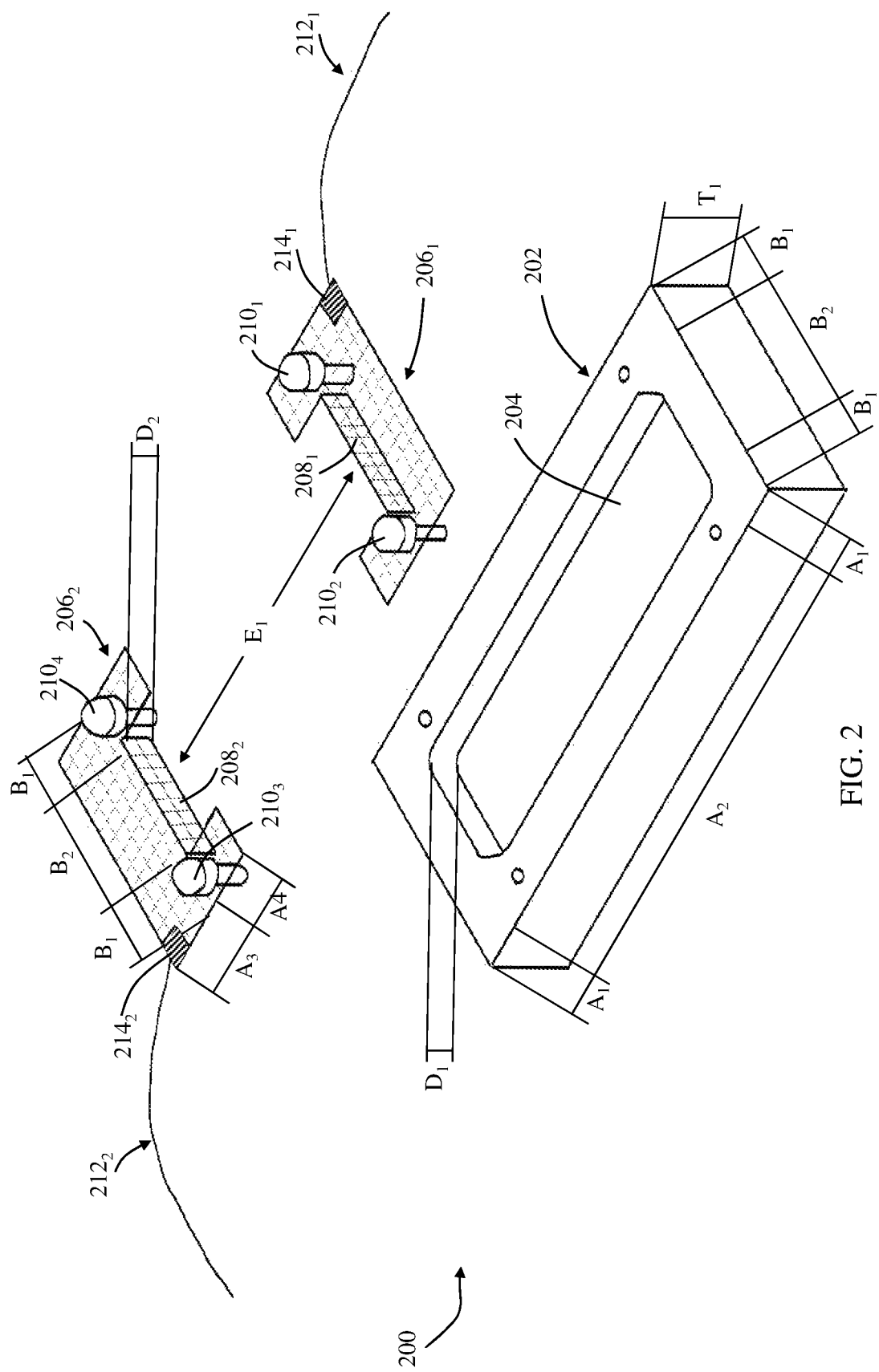
FIG. 2 is a schematic representation of the experimental set-up, including the specimen mold and electrodes.

Referring to FIG. 2 a schematic representation of a test set-up 200 used in the two-point uniaxial EIS testing is shown. A specimen mold 202 preparation was started by using a marine-grade high-density polyethylene (HDPE) frame. The specimen mold shows dimensions A1, A2, B1, B2, T1, and D1. This material provides an electrically insulated mold. In one embodiment, the lengths $A_1$ and $A_2$ of the specimen mold 200 are about 13-mm and about 108-mm, respectively. In one embodiment, the widths $B_1$ and $B_2$ of the specimen mold 200 are about 13-mm and about 32-mm. In one embodiment, the thickness $T_1$ of the specimen mold 200 is about 19-mm. The specimen mold 202 was cut to the desired size using a vertical band saw. A rectangular pocket 204 was then milled into the blank HDPE frame using a computerized numerical control (CNC) milling machine, employing a 13-mm diameter tool (speed: 1300 RPM, feed: 1585 mm/min). In one embodiment the length $A_2$, width $B_2$, and pocket depth $D_1$ of the rectangular pocket 204 is about 108-mm, about 32-mm and about 6-mm. Since the milling tool had a 13-mm diameter, the final specimen holder resulted in a rectangular pocket 204 with rounded corners having a 6.5-mm corner radius. A similar process was performed to manufacture molds with five different pocket depths (3, 5, 6, 10 and 13-mm). The dimensions were measured to ensure conformance to the desired dimensions.

Electrodes $206_1$, and $206_2$, according to one embodiment made of a copper woven wire cloth having about a 0.30-mm wire diameter, were placed at both ends of the specimen mold 202. The electrodes $206_1$, and $206_2$ are defined by lengths $A_3$ and $A_4$, and widths $B_1$ and $B_2$. In one embodiment, the lengths $A_4$ and $A_3$ of the electrodes $206_1$, and $206_2$ are about 13-mm and about 19-mm, respectively. In one embodiment, the widths $B_1$ and $B_2$ of the electrodes $206_1$, and $206_2$ are about 13-mm and about 32-mm, respectively. These rectangular mesh (58 by 32±2 mm) electrodes $206_1$, and $206_2$ were placed on top of the specimen mold 202, each held in place by two plastic screws $210_1$, $210_2$, $210_3$, and $210_4$ respectively. Each electrode $206_1$ and $206_2$ has an embedded segment $208_1$, and $208_2$, respectively. The embedded segments $208_1$, and $208_2$ are a segment of mesh that is notched and bent toward the rectangular pocket 204 in order to make electrical connections with the specimen in the specimen mold 202. The electrodes $206_1$, and $206_2$ are separated by a distance $E_1$. In one embodiment, the separation distance $E_1$ between the embedded segments $208_1$, and $208_2$ is about 95-mm and each embedded segment $208_1$, and $208_2$ has a depth $D_2$ of about 6-mm. Each electrode $206_1$, and $206_2$ has a 154-mm stranded wire $212_1$, and $212_2$ soldered to the mesh at a wire solder location $214_1$, and $214_2$, respectively. The wire solder locations $214_1$, and $214_2$, are located opposite the respective embedded segment $208_1$, and $208_2$.

Figure 3B:
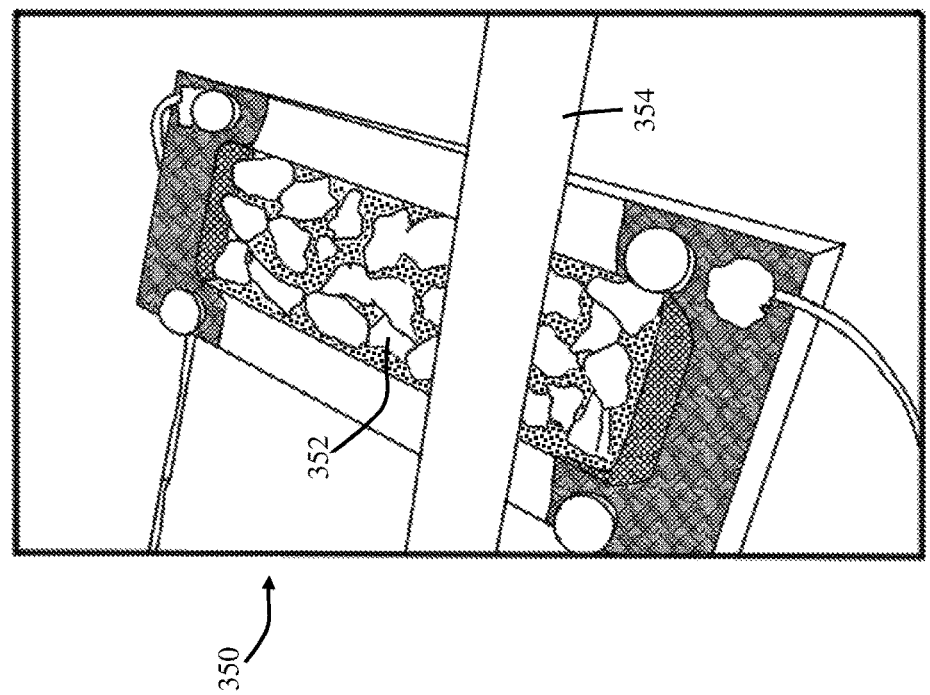
FIG. 3(b) is a perspective of one specimen mold prepared with an emulsified asphalt-aggregate specimen, including a tamping rod.
Figure 3A:
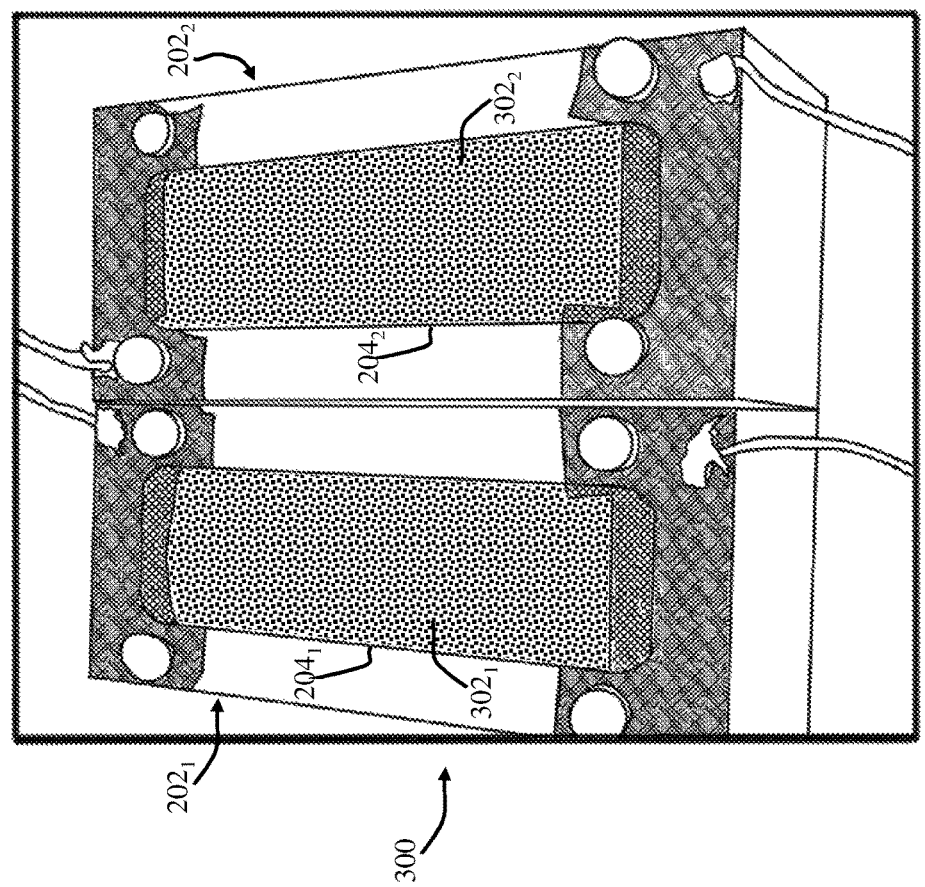
FIG. 3(a) is a perspective of two specimen molds prepared with an emulsified asphalt specimen.

Referring to FIG. 3(a), a perspective drawing of an emulsified asphalt system 300 used in testing is shown. Each specimen mold $202_1$, and $202_2$ was prepared by pouring emulsified asphalt specimens $302_1$, and $302_2$ into the respective rectangular pockets $204_1$, and $204_2$ until the total volume of the rectangular pockets $204_1$, and $204_2$ was filled. Emulsified asphalt specimens for both AE-90S and CRS-2P were cast at five different specimen thicknesses 3, 5, 6, 10 and 13 mm. Emulsified asphalt-aggregate specimens were prepared to replicate typical chip seal emulsified asphalt applications rates, 1.4 and 1.8 L/m$^2$, 4.8 and 6.3 g were equivalent to placing 1.4 and 1.8 L/m$^2$, respectively. The corresponding emulsified asphalt quantities were poured into a 6-mm pocket depth mold. The mold was tilted back and forth to enable the emulsified asphalt to develop a uniform thickness.

Referring to FIG. 3(b), a perspective drawing of an emulsified asphalt-aggregate system 350 used in testing is shown. Following preparation of an emulsified asphalt system 300 (see FIG. 3(a)), the aggregates 352 were spread until a prevalent interlocking mosaic pattern was achieved. The aggregate application rates for limestone and gravel were approximately 10 and 12 kg/m$^2$, respectively. A tamping rod 354 was rolled six times along the longitudinal side of the specimen to provide a thorough, consistent chip embedment and orientation, simulating rolling operations performed during chip seal projects.

One difference between FIGS. 3(a) and 3(b) is the source of moisture (one being from the emulsified asphalt specimens $302_1$, and $302_2$ and one being from the aggregates 352). In particular, the difference is that FIG. 3(a) represents an emulsified asphalt system 300, and FIG. 3(b) represents an emulsified asphalt-aggregate system 350. Both systems have moisture from the emulsified asphalt specimens $302_1$, and $302_2$. Whereas, the emulsified asphalt-aggregate system 350 might or might not have moisture from the aggregate 352.

After the preparation described above, the specimens were immediately connected to the EIS analyzer to acquire the impedance data in an automated fashion at 10-minute intervals for 16 hours. At the same time as the water in the emulsified asphalt was evaporating, the mass of each specimen was constantly measured using a balance. These readings were logged at 1-minute intervals. These electrical properties and mass of the specimens were continually measured until no more mass change was observed (i.e., about 0.0002 g/h). At this point, the specimens were considered completely cured. The experimental procedure was conducted in a 23±0.5° C. and 50±2% relative humidity (RH) environmental chamber.

To better explain the results, moisture content ratio was defined as:

$$MCR = \left(\frac{m_t - m_f}{m_i - m_f}\right) \times 100 \quad (1)$$

where MCR is the moisture content ratio in percentage form, $m_i$ is the initial specimen mass, in grams, $m_t$ is the specimen mass at any given curing time, in grams, and $m_f$ is the final specimen mass (i.e., when the specimen is completely cured), in grams.

Figure 4B:
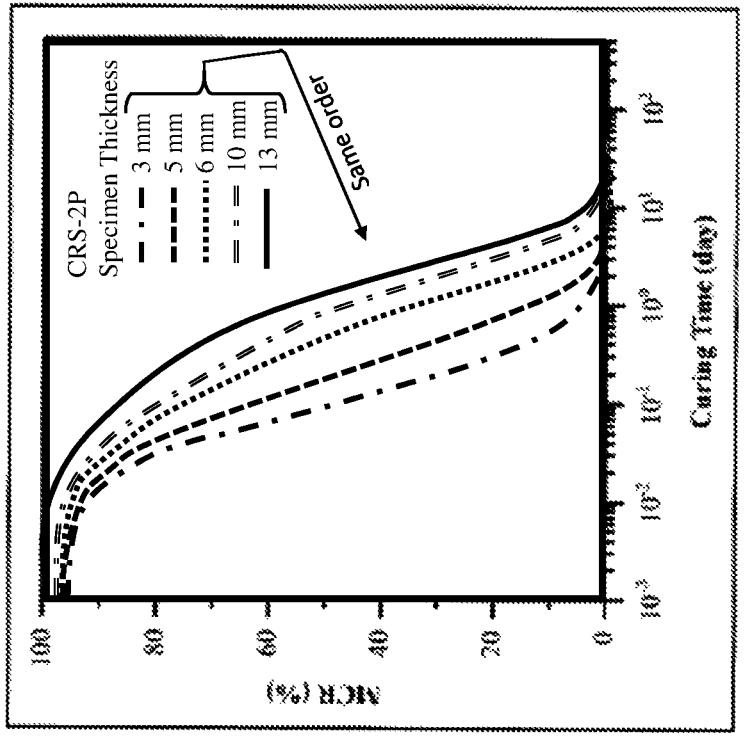
FIG. 4(b) is a graph of moisture content ratio (MCR) vs. curing time for CRS-2P emulsified asphalt specimens of various thicknesses.
Figure 4A:
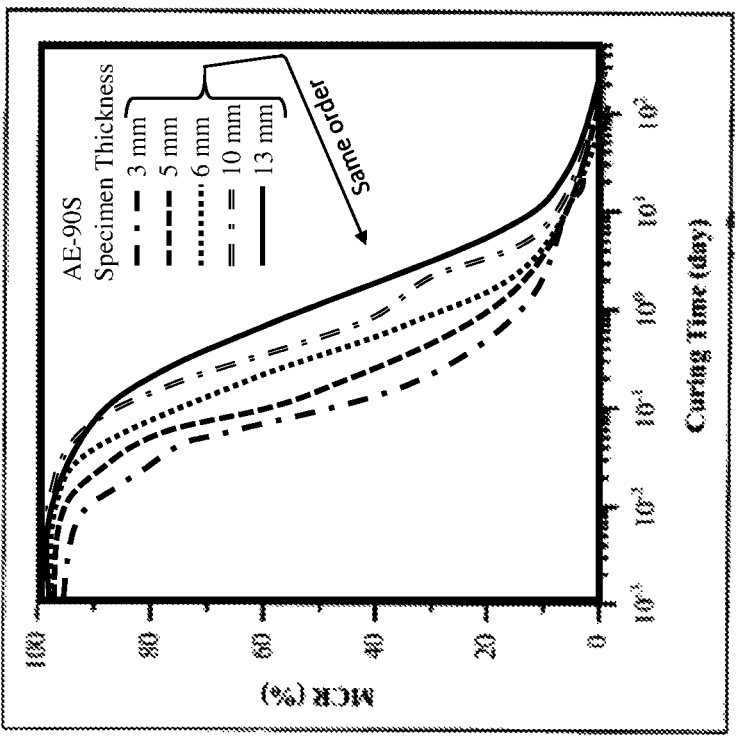
FIG. 4(a) is a graph of moisture content ratio (MCR) vs. curing time for AE-90S emulsified asphalt specimens of various thicknesses.

Four typical emulsified asphalt-aggregate combinations were tested using two emulsified asphalt application rates, 1.4 and 1.8 L/m2, and two aggregate moisture conditions, oven dry (OD) and saturated-surface dry (SSD). FIGS. 4(a) and 4(b) are graphs of MCR (%) vs. curing time (days for the emulsified asphalt specimens of different thicknesses). The cationic emulsified asphalt cured more rapidly than did the anionic emulsified asphalt; all the CRS-2P specimens were cured at 15% MCR by 5 days, whereas the AE-90S specimens achieved the same condition by 10 days. For both emulsified asphalt types, the thicker the emulsified asphalt film, the longer the curing time.

Figure 5B:
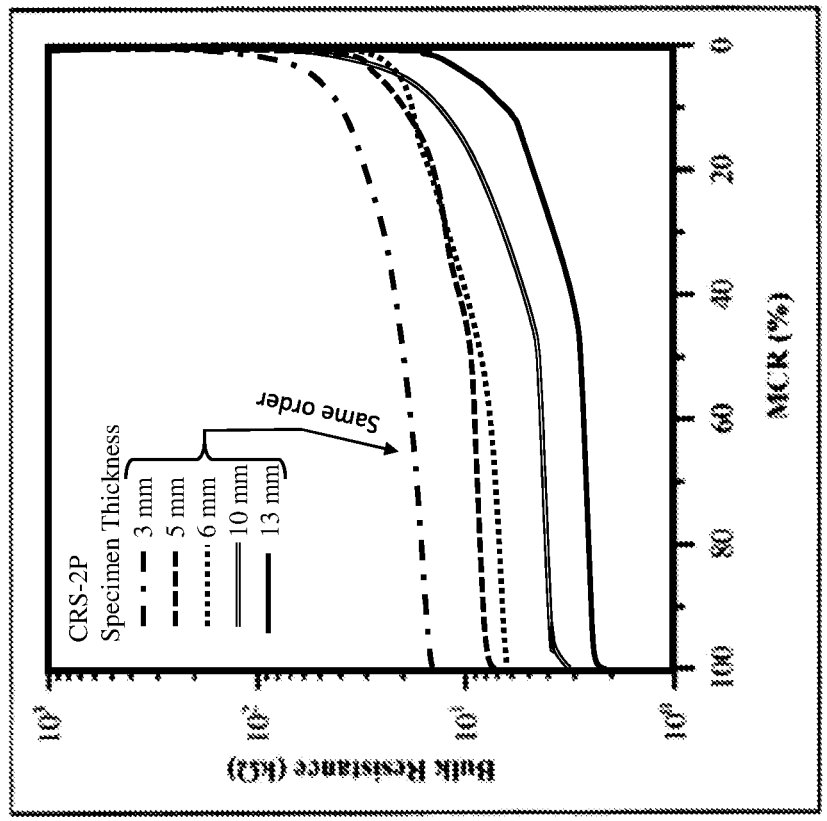
FIG. 5(b) is a graph of bulk resistance vs. moisture content ratio (MCR) for CRS-2P emulsified asphalt specimens of various thicknesses.
Figure 5A:
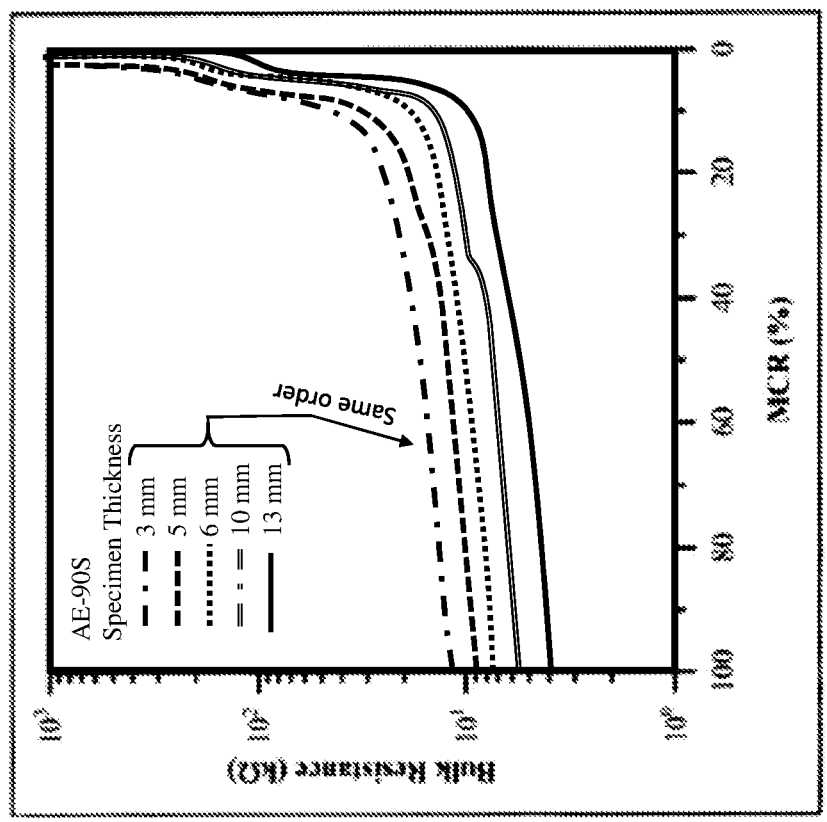
FIG. 5(a) is a graph of bulk resistance vs. moisture content ratio (MCR) for AE-90S emulsified asphalt specimens of various thicknesses.

Now diverting attention to the bulk resistance of the emulsified asphalt specimens, the resistance increased during the curing process, as discussed above. The results are shown in FIGS. 5(a) and 5(b), where bulk resistance is shown vs. moisture content for the two different emulsified mixtures. This electrical response reflects both the volume and the connectivity of the water molecules and its ionic species as the emulsified asphalt cures. However, it is evident that the specimen thickness had a dominant effect on the electrical response. Thicker specimens exhibited lower bulk resistance measurements. This electrical response is mainly attributed to the influence of the cross-sectional area on the diffusion rate of water and the ions' ability to move freely and carry the electric current, as can be appreciated by a person having ordinary skill in the art. The same is true for any material of uniform cross-section has a resistance that varies inversely with its cross-sectional area.

Resistivity of a homogenous material, a property inherent to a material, is calculated by dividing the product of resistance and cross-sectional area by the distance between electrodes. However, the cross-sectional area of a chip seal is not homogenous and can significantly vary due to the quantity of emulsified asphalt, quantity of aggregate, nominal aggregate size, aggregate gradation, percent of voids filled, and rolling operation protocol (i.e., rolling type and pattern, number of coverages, aggregate embedment depth). Given this possible variation, a normalized resistance index (NRI) was used to reduce the cross-sectional area characteristics of the chip seal system, as described in the equation below $$NRI = \frac{R_t}{R_i}$$

where NRI is the normalized resistance index, which is unitless, $R_t$ is the bulk resistance at any given MCR measured in kΩ, and $R_i$ is the initial bulk resistance at 100% MCR also measured in kΩ.

Figure 6B:
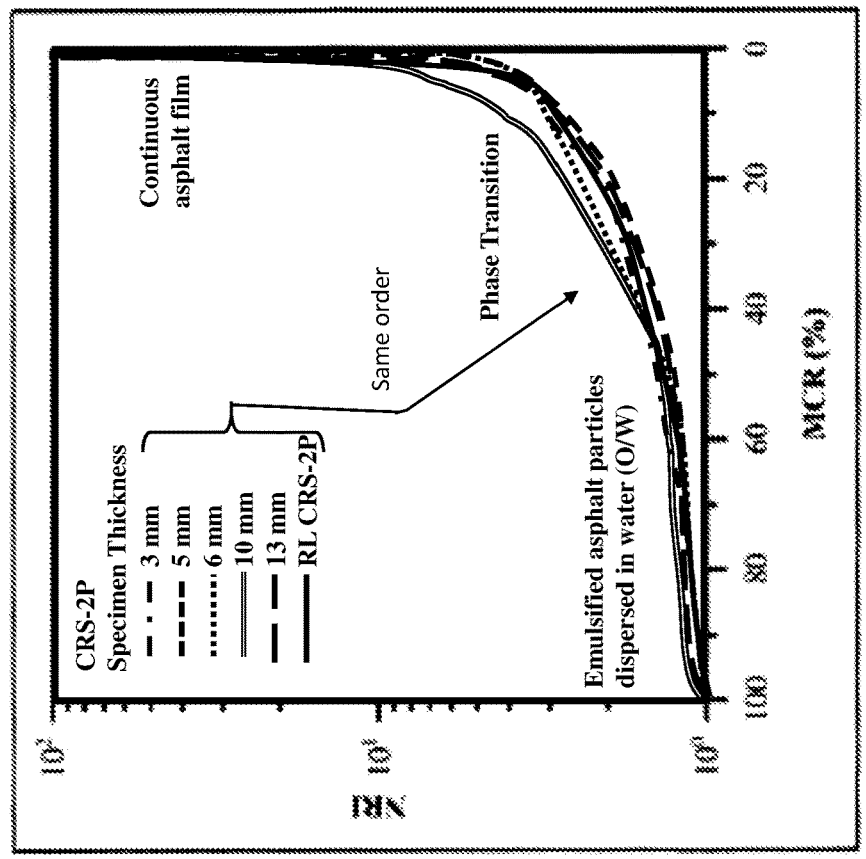
FIG. 6(b) is a graph of normalized resistance index (NRI) vs. moisture content ratio (MCR) for CRS-2P emulsified asphalt specimens of various thicknesses.
Figure 6A:
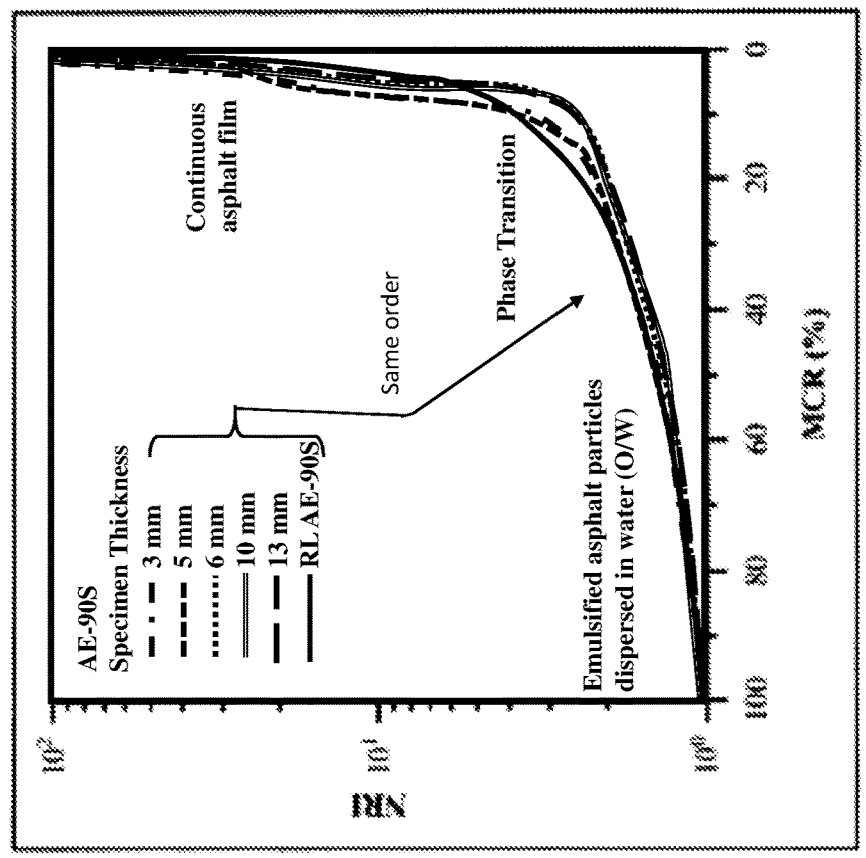
FIG. 6(a) is a graph of normalized resistance index (NRI) vs. moisture content ratio (MCR) for AE-90S emulsified asphalt specimens of various thicknesses.

Referring to FIGS. 6(a) and 6(b), graphs of NRI vs. MCR are shown for the two emulsified mixtures. There is a significant increase in NRI after the MCR is considerably reduced (down to about 20%), indicating emulsified asphalt phase transition from emulsified asphalt particles dispersed in water to a continuous asphalt film. The normalized electrical response is well correlated to the amount of moisture remaining in the chip seal system for each type of emulsified asphalt. Table 1 provides statistical analysis of the normalized measurements for all specimen thicknesses and indicates the coefficients of determination (R2) are 0.98 and 0.97, for AE-90S and CRS-2P, respectively.

TABLE 1

Regression analysis between normalized resistance index and moisture content ratio for emulsified asphalt specimens

| Emulsified Asphalt | Regression Analysis | |
|---|---|---|
| | Regression Line (RL) | $R^2$ |
| AE-90S | $\sqrt{MCR} = 0.114\left(\frac{1}{NRI}\right) - 0.096$ | 0.98 |
| CRS-SP | $\sqrt{MCR} = 0.096\left(\frac{1}{NRI}\right) - 0.043$ | 0.97 |

TABLE 2

Emulsified asphalt-aggregate specimens

| Emulsified Asphalt-Aggregate Combination | Emulsified Asphalt Application Rate | Aggregate Application Rate | Aggregate Moisture Condition |
|---|---|---|---|
| AE-90S Limestone (AL) | 1.4 L/m$^2$ | 10 kg/m$^2$ | Oven dry |
| | | | Saturated-surface dry |
| | 1.8 L/m$^2$ | | Oven dry |
| | | | Saturated-surface dry |
| CRS-2P Limestone (CL) | 1.4 L/m$^2$ | | Oven dry |
| | | | Saturated-surface dry |
| | 1.8 L/m$^2$ | | Oven dry |
| | | | Saturated-surface dry |
| AE-90S Gravel (AG) | 1.4 L/m$^2$ | 12 kg/m$^2$ | Oven dry |
| | | | Saturated-surface dry |
| | 1.8 L/m$^2$ | | Oven dry |
| | | | Saturated-surface dry |
| CRS-2P Gravel (CG) | 1.4 L/m$^2$ | | Oven dry |
| | | | Saturated-surface dry |
| | 1.8 L/m$^2$ | | Oven dry |
| | | | Saturated-surface dry |

The emulsified asphalt-aggregate test results are provided below. NRI can quantify the amount of curing that occurs in four typical emulsified asphalt-aggregate combinations. As detailed in Table 2, 16 different emulsified asphalt-aggregate combination specimens were tested.

Figure 7B:
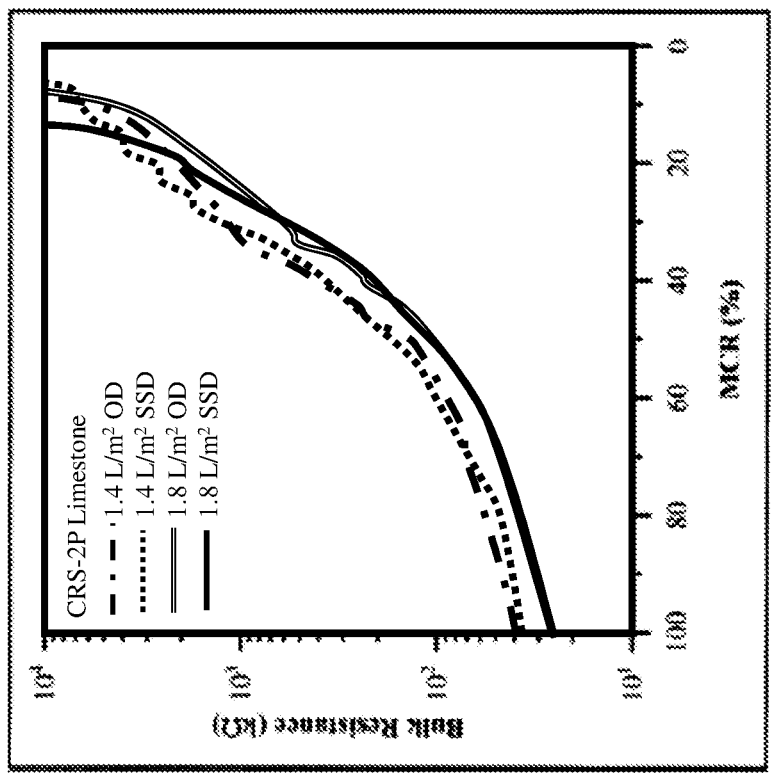
FIG. 7(b) is a graph of bulk resistance vs. moisture content ratio (MCR) for a CRS-2P emulsified asphalt-aggregate mixture at various application rates.
Figure 7A:
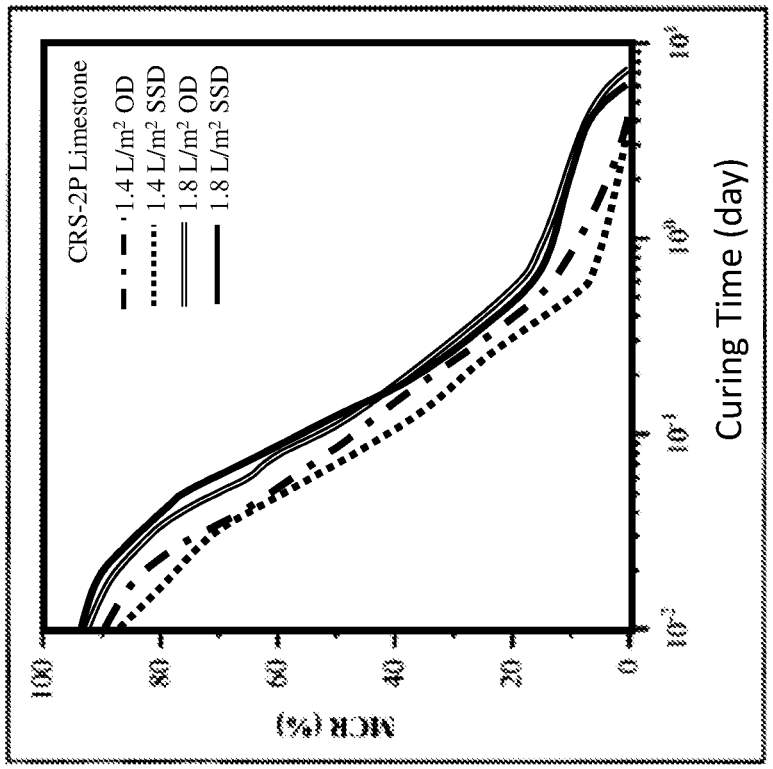
FIG. 7(a) is a graph of moisture content ratio (MCR) vs. curing time for a CRS-2P emulsified asphalt-aggregate mixture at various application rates.

Referring to FIG. 7(a) a graph of MCR vs. curing time (days) is provided while FIG. 7(b) provides a graph of bulk resistance vs. MCR for the CRS-2P limestone (CL) combination shown in Table 2. In FIG. 7(a), specimens containing 1.4 L/m$^2$ of emulsified asphalt cured more rapidly than did specimens made with 1.8 L/m$^2$ of emulsified asphalt. These results highlight that any single variable can delay or accelerate the curing process. FIG. 7(b) shows that a lower electrical resistance measurement was observed in specimens containing 1.8 L/m$^2$ of emulsified asphalt.

The curing of emulsified asphalts is a physical-chemical process governed by the energy differences among the forces acting between the dispersed asphalt particles which include electrostatic forces and stearic repulsion interactions, as well as, water evaporation and diffusivity. Such interactions in the final application depend on the emulsified asphalt formulation, aggregate chemistry and surface area, environmental conditions, mechanical rolling (compaction) and other less quantifiable factors. Hence, using electrical properties to quantify emulsified asphalt curing times can be very beneficial to simplify the curing process evaluation of chip seals and various emulsified asphalt applications.

The phase transition of the dispersed asphalt particles present in the emulsion to the continuous binder phase in the pavement is a key process in all the applications of emulsified asphalt. Emulsified asphalts are graded on how readily they cure in contact with the aggregates used in road construction; different curing properties are suitable for different applications. Rapid-setting (RS) grades are the fastest curing emulsified asphalts, slow-setting (SS) grades the least, and medium-setting (MS) grades have intermediate curing characteristics. To date, there is no effective quantitative measurement technique to assess the curing process of emulsified asphalts in the field. The findings presented in the present disclosure have demonstrated that electrical properties can be used to detect phase transition and continuous binder film development of emulsified asphalts. Electrical measurement techniques can provide a rapid, nondestructive indication of the amount of curing that has occurred in various emulsified asphalt applications. Additionally, electrical properties can be employed to grade emulsified asphalts.

Based on these results, a normalized resistance index (NRI) or changes in the bulk resistance can be correlated to the amount of moisture in the chip seal system. According to one embodiment, a change in bulk resistance of at least about 10 times from an initial state to a subsequent cured state is sufficient to indicate proper amount of curing. Therefore, a processing unit can be employed to periodically (i.e., predetermined time intervals) measure the bulk resistance (i.e., the minimum impedance at each time interval), with the first recordation of the bulk resistance to be used as a referenced until the bulk resistance is at least about 10 times the reference.

Figure 8:
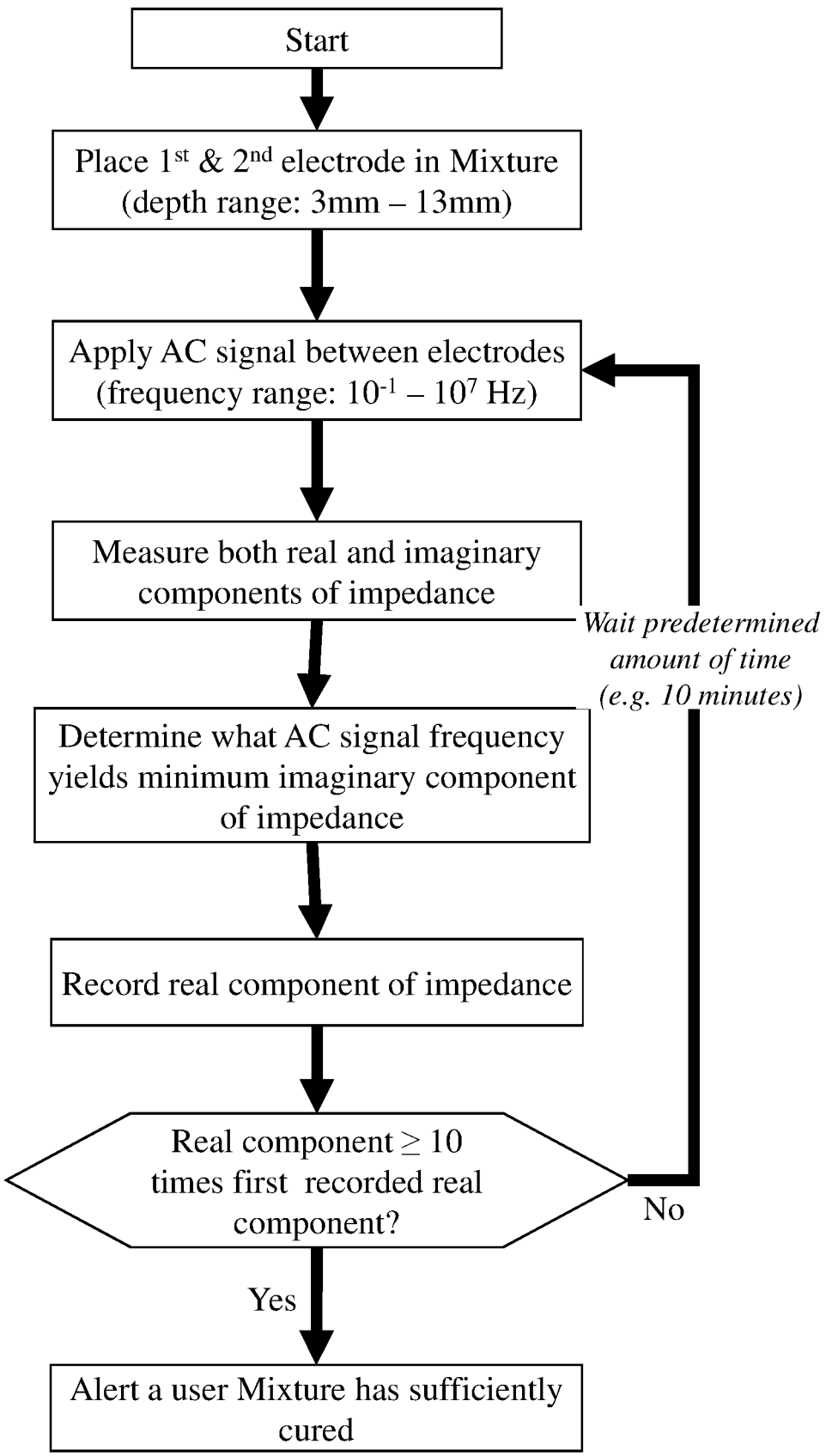
FIG. 8 is a flow-chart showing the steps of one embodiment for determining moisture content of an emulsified asphalt-aggregate system.

Referring to FIG. 8, a flow-chart showing the steps of one embodiment for determining moisture content of an emulsified asphalt-aggregate system is provided. The moisture content of an emulsified asphalt-aggregate system, or Mixture for short, can be determined by following a series of steps, starting with embedding a first and second electrode in the emulsified asphalt-aggregate system (Mixture). The first electrode should be embedded to a first depth such that it is at least three millimeters below the top surface of the Mixture, and no greater than thirteen millimeters below the top surface of the Mixture. The second electrode should be embedded to a second depth such that it is at least three millimeters below the top surface of the Mixture, and no greater than thirteen millimeters below the top surface of the Mixture. Once the first and second electrode have been embedded in the Mixture, an alternating current (AC) signal should be applied between the first and second electrode. The AC signal will have a frequency range between about $10^{-1}$ and about $10^7$ Hz at a peak-to-peak voltage ($V_{PP}$) of about 500 mv. Once the AC signal has been applied between the first and second electrode the impedance should be measured. The impedance has a real component, which represents the resistance between the first and second electrode, and an imaginary component, which represents the capacitance between the first and second electrode. The next step is to determine which AC signal frequency, from the range between about $10^{-1}$ and about $10^7$ Hz, yields the minimum imaginary component of impedance. Next, the real component value of the impedance should be recorded. Once the real component value of impedance has been recorded, it should be compared to the first recorded real component value of impedance. If the recorded real component value of impedance is about ten times greater than the first recorded real component value of impedance, then a user should be alerted that the Mixture has sufficiently cured. If the recorded real component value of impedance is not about ten times greater than the first recorded real component value of impedance, then the steps of applying an AC signal, measuring and recording the real and imaginary component of impedance, and comparing to the first recorded real component value of impedance should be repeated at a predetermined time interval.

Those having ordinary skill in the art will recognize that numerous modifications can be made to the specific implementations described above. The implementations should not be limited to the particular limitations described. Other implementations may be possible.

The invention claimed is:

1. A method of determining moisture content in an emulsified asphalt-aggregate system, comprising:
    A) placing a first electrode in the emulsified asphalt-aggregate system (Mixture) at a first depth;
    B) placing a second electrode in the Mixture at a second depth;
    C) applying an alternating current (AC) signal between the first electrode and the second electrode at a plurality of frequencies;
    D) measuring impedance, comprising of a real component representing resistance between the first electrode and the second electrode and an imaginary component representing capacitance between the first electrode and the second electrode;
    E) determining a frequency ($f_0$) which yields a minimum measured impedance based on the plurality of frequencies;
    F) recording the minimum measured impedance associated with $f_0$;
    G) repeating steps C-F at a predetermined time interval until the recorded minimum measured impedance is about 10 times of a first recorded minimum measured impedance; and
    H) alerting a user that the Mixture has sufficiently cured.

2. The method of claim 1, wherein the first depth is ranging from about 3 mm to about 13 mm from a top surface of the Mixture.

3. The method of claim 1, wherein the second depth is ranging from about 3 mm to about 13 mm from the top surface of the Mixture.

4. The method of claim 1, wherein the AC signal has a frequency range between about $10^{-1}$ and about $10^7$ Hz.

5. The method of claim 1, wherein the AC signal has a peak-to-peak voltage of about 500 mv.

6. The method of claim 1, wherein the first electrode and the second electrode are made of copper woven wire cloth.

7. The method of claim 2, wherein the first and second electrodes each have about 0.3 mm diameter.

8. The method of claim 6, wherein the woven wire cloth represent rectangular meshes.

9. The method of claim 4, wherein the rectangles are about 58 by about 32±2 mm.

10. The method of claim 5, wherein the electrodes are separated by between about 50 mm to about 150 mm.

11. A System for determining moisture content in an emulsified asphalt-aggregate system, comprising:
    a first electrode adaptable to be placed in the emulsified asphalt-aggregate system (Mixture) at a first depth;
    a second electrode adaptable to be placed in the Mixture at a second depth;
    an alternating current (AC) source adaptable to provide an AC signal between the first electrode and the second electrode;
    an impedance measurement device adaptable to measure impedance between the first electrode and the second electrode, the impedance comprising of a real component representing resistance between the first electrode and the second electrode and an imaginary component representing capacitance between the first electrode and the second electrode;
    a processing unit configured to:
        A) apply the AC signal between the first electrode and the second electrode at a plurality of frequencies,
        B) measure impedance,
        C) determine a frequency ($f_0$) which yields a minimum measured impedance based on the plurality of frequencies,
        D) record the minimum measured impedance associated with $f_0$,
        E) repeat steps A-D at a predetermined time interval until the recorded minimum measured impedance is about 10 times of a first recorded minimum measured impedance, and
        F) alert a user that the Mixture has sufficiently cured.

12. The system of claim 11, wherein the first depth is ranging from about 3 mm to about 13 mm from a top surface of the Mixture.

13. The system of claim 11, wherein the second depth is ranging from about 3 mm to about 13 mm from the top surface of the Mixture.

14. The system of claim 11, wherein the AC signal has a frequency range between about $10^{-1}$ and about $10^7$ Hz.

15. The system of claim 11, wherein the AC signal has a peak-to-peak voltage of about 500 mv.

16. The system of claim 11, wherein the first electrode and the second electrode are made of copper woven wire cloth.

17. The system of claim 12, wherein the first and second electrodes each have about 0.3 mm diameter.

18. The system of claim 16, wherein the woven wire cloth represent rectangular meshes.

19. The system of claim 14, wherein the rectangles are about 58 by about 32±2 mm.

20. The system of claim 15, wherein the electrodes are separated by between about 50 mm to about 150 mm.

* * * * *